United States Patent [19]

Fischer

[11] Patent Number: Plant 5,543

[45] Date of Patent: Aug. 27, 1985

[54] AFRICAN VIOLET PLANT NAMED MARGUERITE

[75] Inventor: Arnold Fischer, Hanover, Fed. Rep. of Germany

[73] Assignee: Pan American Plant Company, Parrish, Fla.

[21] Appl. No.: 539,935

[22] Filed: Oct. 7, 1983

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Schwartz, Jeffery, Schwaab, Mack, Blumenthal & Koch

[57] ABSTRACT

A new and distinct cultivar of African violet particularly characterized by its large pink ruffled flowers that are star-shaped and actinomorphic rotate, compact rosette habit, with the flowers being carried on upright peduncles, floriferous habit, and its pleasantly contrasting dark green foliage.

1 Drawing Figure

1

The present invention comprises a new and distinct cultivar of African violet plant, botanically known as *Saintpaulia ionantha,* and hereinafter referred to by the cultivar name Marguerite.

The new cultivar was referred to during the breeding and selection process by the designation V7-H68-P, and is a product of a planned breeding program. The basic objective of the breeding program was to create a new African violet cultivar having an abundance of large pink star-shaped ruffled flowers above symmetrical dark green foliage.

The new cultivar was originated from a cross made by Arnold Fischer in a controlled breeding program in Hannover, Germany in 1976. The male and female are unknown at this time.

Marguerite was discovered and selected by Arnold Fischer as a flowering plant within the progeny of the stated cross in a controlled environment in Fallbrook, Calif. in 1977. Asexual reproduction of the new cultivar by leaf cuttings, as performed by me at West Chicago, Ill., and Parrish, Fla., has demonstrated that the combination of characteristics as herein disclosed for the new cultivar are firmly fixed and retained through successive generations of asexual reproduction.

Marguerite has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Marguerite which in combination distinguish this African violet as a new and distinct cultivar:

(1) Large pink ruffled flowers that are star-shaped and actinomorphic rotate.

(2) Compact rosette habit, with flowers on upright peduncles.

(3) Suitable for production in 10 cm. pots, flowering in 9 to 13 weeks depending upon growing conditions.

(4) Very floriferous, with flowers continuing to open for many weeks after onset of flowering.

(5) Dark green pubescent foliage, the abaxial side purple, and a crenate leaf margin.

The new cultivar is most similar to Pink Lady, disclosed in applicant's U.S. Plant Pat. No. 5,065. Marguerite is principally distinguished from Pink Lady by its darker green foliage, which isn't as "quilted" in appearance, and its lighter pink, ruffled actinomorphic flower.

2

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 5000 foot candles of natural light at approximately 11:30 A.M. in Parrish, Fla.

Botanical classification: *Saintpaulia ionantha,* Ramat, cv. Marguerite.

Parentage:

*Male parent.*—Unknown.

*Female parent.*—Unknown.

Propagation: The new cultivar holds its distinguishing characteristics through successive propagations by leaf cuttings.

Plant: From 4 cm. to 8 cm. tall when grown in pots, and approximately 22 cm. in diameter when fully grown. The growth rate is vigorous, and the general shape of the fully grown plant is round.

Leaves:

*Quantity.*—Abundant.

*Shape.*—Cordate with crenate margin.

*Diameter.*—65–75 mm.

*Texture.*—Pubescent, glossy.

*Ribs and veins.*—Pinnate.

*Color (upperside).*—147A.

*Color (underside).*—Ranging from 187A on young leaves to 187D on old leaves.

*Petioles.*—2–7 cm. In length.

Flowers:

*Buds.*—Size: Up to 1 cm.×1 cm. Shape: Round. Rate of opening: Normal. Color: 56A with greenish areas.

*Sepals.*—Shape: Lanceolate. Color: 182B with show of 147D.

*Phyllaries.*—Two; lanceolate. Color: 147B.

*Calyx.*—Shape: Funnel. Size: About 12 mm. in diameter. Aspect: Hairy.

*Peduncle.*—Length: 2–5 cm. Character: Rigid. Color: 184B with show of 147D.

*Individual flowers.*—Number of petals: Five (5). Size: 35–42 mm. Diameter and 12 mm. deep. Shape: Flower is cup-shaped when bloom first opens, becoming flat as it matures. Color: Upperside: 55D to 56A. Underside: 56D. Flowers fade slightly with age. Color varies with temperature, amount of light, and fertilizer, and other growing conditions. Borne: In a cyme on 20–55 mm. peduncles. Flowering habit: Flowers profusely and intermittently year round with blooms lasting 2–3 weeks after which petals dry up but do not drop. Finishes in 9–13 weeks when a 2¼" plantlet is placed in a 10 cm. pot.

*Reproductive organs.*—Stamens: Five, borne singly surrounding the ovary; anthers basifixed. Anthers: 2 mm.×2 mm., Yellow. Filaments: 2–3 mm., Yellow. Pollen Color: Yellow. Pistels: Number: One (1). Styles: One (1), 6–8 mm. long. Stigma: White, sticky. Ovaries: Superior.

*Roots.*—Fiberous, fine.

*Disease resistance.*—No African violet diseases observed to date.

General observations:

Marguerite is a new and distinct African violet having large flowers held aloft on erect peduncles above the dark green foliage, forming a massive colorful bouquet. The single actinomorphic rotate flower bears five petals all with ruffled margins. Marguerite may be finished in 9–13 weeks from a 2¼" plant in a 10 cm. pot in a controlled environment.

I claim:

1. A new and distinct cultivar of African violet named Marguerite, as described and illustrated, and particularly characterized by its large pink ruffled flowers that are star-shaped and actinomorphic rotate; compact rosette habit, with the flowers being carried on upright peduncles; floriferous habit, and its pleasantly contrasting dark green foliage.

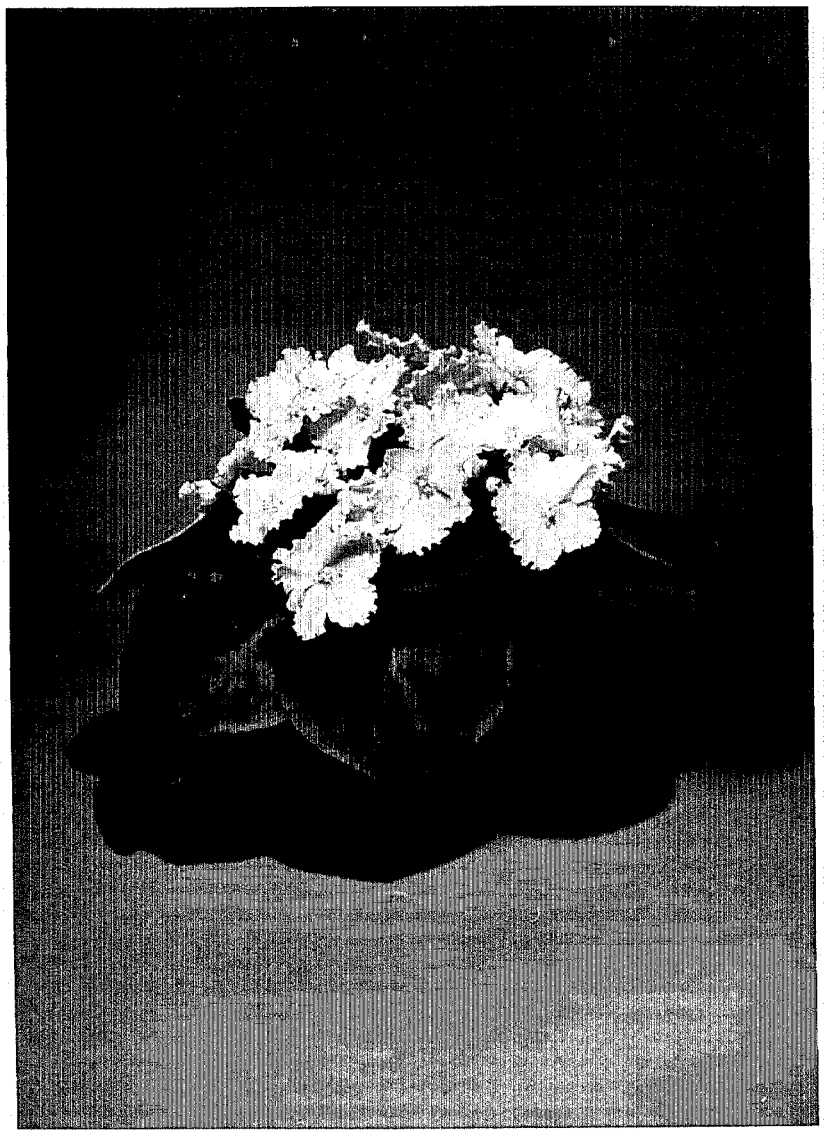

* * * * *